US005831035A

United States Patent [19]

Timms

[11] Patent Number: 5,831,035

[45] Date of Patent: Nov. 3, 1998

[54] ANTIBODY AGAINST HUMAN ENDOMETRIAL STROMAL CELL GLYCOPROTEIN

[75] Inventor: Kathy L. Timms, Columbia, Mo.

[73] Assignee: Curators of the University of Missouri, Columbia, Mo.

[21] Appl. No.: 328,905

[22] Filed: Oct. 25, 1994

[51] Int. Cl.[6] .......................... C07K 16/18; G01N 33/53

[52] U.S. Cl. .................................... 530/389.1; 530/388.2; 530/850; 436/510; 436/65

[58] Field of Search .................................... 436/510, 814, 436/906, 65; 530/388.2, 388.23, 850, 388.24, 388.85, 389.2, 389.1; 435/7.21, 806

[56] References Cited

U.S. PATENT DOCUMENTS 4,489,166 12/1984 Joshi ........................................ 436/510

OTHER PUBLICATIONS

Zucker et al., 1992. Immunoassay of type IV collagenase/gelatinase (MMP–2) in human plasma, J. Immunological Methods 148:189–198.

Bell, SC "Purification of human secretory pregnancy–associated . . . " *Hum Reprod* 1:313–318, (1986).

Bolen et al. "Reactive and neoplastic serosal tissue. A light–microscopic, ultrastructural and immunocytochemical study" *Am J Surg Path* 10:34–47 (1986).

Cornillie et al., "Expression of endometrial protein PP14 in pelvic and ovarian endometriotic implants" *Hum Reprod* 6:1141–1415 (1991).

Critchley et al., "Role of the ovary in the synthesis of placental protein–14" *J Clin Endocrincol Metab* 75:97–100 (1992).

Daly et al., "Prolactin production during in vitro decidualization of proliferative endometrium" *Am J Obstet Gynecol* 145: 672–8 (1983).

Haining et al., "Epidermal growth factor in human endometrium: proliferative effects in culture and immunocytochemical . . . " *Hum Reprod* 6:1200–5 (1991).

Hillam et al., "Local antibody production against the murine toxin of Yersinia pestis in a golf ball–induced granuloma" *Infect Immun* 10:458–463 (1974).

Isaacson et al., "Production and secretion of complement component 3 by endometriotic tissue" *J Clin Endocrin Metab* 69:1003–9 (1989).

Joshi et al., "Detection and synthesis of a progestagen–dependent protein in human endometrium" *J Reprod Fertil* 59:273–85 (1980).

Joshi SG, "Progestin–dependent human endometrial protein: a marker for monitoring human endometrial function" *Adv Exp Med Biol* 230:167–86 (1986).

Julkunen et al., "Identification by hybridization histochemistry of human endometrial cells expressing mRNA's . . . " *Mol Endocrinol* 4:700–7 (1990).

Julkunen et al., "Complete amino acid sequence of human placental protein 14: a progresterone–regulated uterine protein . . . " *Proc. Natl Acad Science USA* 85:8845–8849 (1988).

Knudsen KA, "Proteins transferred to nitrocellulose as immunogens" *Anal Biochem* 147:285–288 (1985).

Koistinen et al., "Placental protein 12 is a decidaul protein that binds somatomedin and has an identical N–terminal amino acid . . . " *Endocrinology* 118:1475–78 (1990).

Kruitwagen et al., "Immunocytochemical marker profile of endometriotic epithelial, endometrial epithelia, and mesothelial cells . . . " *European J Obstet Gynecol Reprod Biol* 41:215–223 (1991).

Lessey et al., "Immunohistochemical analysis of estrogen and progesterone receptors in endometrisosis: comparison with normal . . . " *Fertil Steril* 51:409–415 (1989).

Maslar et al., "Prolactin production by human endometrium during the normal menstrual cycle" *Am J Ostet Gynecol* 135:751–754 (1979).

McRae et al., "Immunohistochemical identification of prolact and 24K protein in secretory endometrium" *Fertil Steril* 45:643–48 (1986).

Melega et al., "Tissue factors influencing growth and maintenance of endometriosis" *Ann NY Acad Sci* 622:257–65 (1991).

Osteen et al., "Development of a method to isolate and culture highly purified populations of stromal and epithelial cells . . . " *Fertil Steril* 52:965–72 (1989).

Riittinen L, "Serous ovarian cyst fluids contain high levels of endometrial placental protein 14" *Tumor Biol* 13:175–9 (1992).

Seppala et al., "Endometrial proteins: A reappraisal" *Hum Reprod* 7:31–8 (1992).

Sharpe et al., "Detection of a progesterone–induced secretory protein synthesized by theuteri but not the endometriotic . . . " *Fertil Steril* 55:403–10 (1991).

Sharpe et al., "Proliferative and morphogenic changes induced by the coculture of rat uterine and peritoneal cells . . . " *Fertil Steril* 58:1220–9 (1992).

Sharpe et al., "Polypeptides synthesized and released by rat endometriotic tissue differ from those of the uterine . . . " *Biol Reprod* 48:1334–1340 (1993). (Jun. 1993).

(List continued on next page.)

*Primary Examiner*—Paula K. Hutzell
*Assistant Examiner*—James L. Grun
*Attorney, Agent, or Firm*—Kohn & Associates

[57] ABSTRACT

An antibody to the purified and isolated glycoprotein and functional analogs thereof characterized by being progesterone induced and estradiol inhibited secretory glycoprotein specifically from stromal cells of endometrial origin. The protein has the molecular weight of 70,000 daltons as determined by two-dimensional SDS-PAGE polyacrylamide gel electrophoresis and has an isoelectric point of 5.7.

1 Claim, 2 Drawing Sheets

OTHER PUBLICATIONS

Sharpe et al., "Polypeptides synthesized and released by human endometriosis tissue differ from those of the uterine . . . " *Fertil Steril* 60:839–51 (1993). (Nov. 1993).

Sharpe et al., "Synthesis and secretion of the progeserone–induced uterine protein, PUP–1, during early pregnancy in the rat" *Soc Study of Reprod* P–26, Ann Arbor, MI (1994).

Telimaa et al., "Elevated serum levels of endometrial secretory protein PP14 in patients with advanced endometriosis" *Am J Obstet Gynecol* 161:866–71 (1989).

Vernon et al., "Classification of endometriotic implants by morphologic appearance and capacity to synthesize prostaglandin F" *Fertil Steril* 801–806 (1986).

Vierikko et al., "Steroidal regulation of endometriosis tissue: lack of induction of . . . " *Fertil Steril* 43:218–224 (1985).

Wahlstrom et al., "Placental protein 12 (PP12) is induced in the endometrium by progesterone" *Fertil Steril* 41:781–4 (1984).

Weibel ER, Stereological Methods. In: *Practical Methods for Biological Morphometry*, vol. 1, New York: Academic Press; 33–45 (1979).

Sharpe et al, Jul. 1993. Synthisis and secretion of the progesterone–induced utenne protein, PUP–1, during early pregnancy in the rat. Biol. Reprod. 48 (Suppl. 1): 117, Abstract #233.

Sharpe et al, Jun. 1994. Immunolocalization of progesterone–induced uterine protein, PUP–1, in human endometrium and in endometrial epithlial and stromal cell cultures. Biol. Reprod. 50 (Suppl. 1): 61, Abstract #26.

Campbell, 1987. Monoclonal Antibody Technology. The Production and Characterization of Rodent and Human Hybridomas. Elsevier, Amsterdam. p. 29.

ANTIBODY AGAINST HUMAN ENDOMETRIAL STROMAL CELL GLYCOPROTEIN

GRANT REFERENCE

The research carried out in connection with this invention was supported in part by a grant from the National Institute of Health No. DHHS NICHD R29HD29026-01. The Government has certain rights in this invention.

TECHNICAL FIELD

The present invention relates to a field of fertility and more particularly, to means and methods for determining endometrial receptivity for a fertilized egg.

BACKGROUND OF THE INVENTION

There are many issues involved with the evaluation of a women's fertility. Production and availability of a egg, fertilization of the egg, and other issues involving the physiology of the egg are involved. Another general issue is the nature of the receptivity of the endometrium. If not receptive to implantation, implantation of a fertilized egg may not occur or may occur in an abnormal manner. If receptive, implantation is optimized. Accordingly, it would be desirous to have a diagnostic tool for determining endometrial receptivity.

The composition of uterine secretions is of considerable interest because of how they may effect reproductive processes such as sperm migration, embryo transport and implantation in the uterine endometrium. Uterine fluid, as it exists in vivo, is a mixture of proteins synthesized and secreted by the endometrium, proteins transferred across the endometrium from the blood stream or adjacent cells and proteins from the oviduct and/or cervix. As a result of progesterone (P) stimulation, the secretory stage human endometrium synthesizes and secretes specific proteins including pregnancy-associated endometrial $\alpha_1$-globulin ($\alpha_1$-PEG), pregnancy-associated endometrial $\alpha_2$-globulin ($\alpha_2$-PEG), prolactin (PRL) and progesterone-induced uterine protein-1 (PUP-1)[Seppela et al., 1992; Maslar and Riddick, 1979; Sharpe et al., 1993]. Although $\alpha_1$-PEG has been described by different names in the literature including placental protein 12 [PP12] and endometrial protein 14 [EP14], subsequently analysis has identified this protein as insulin-like growth factor binding protein-1 (IGFBP-1) [Koistinen et al., 1992].

Messenger RNA encoding human IGFBP-1 and corresponding protein has been identified in secretory stage endometrial stromal cells but not secretory stage epithelial cells nor any proliferative stage endometrial cells [Julkunen et al., 1990; Wahlstrom et al, 1984]. Several forms of nomenclature also appear in the literature for $\alpha_2$-PEG including placental protein [PP14], endometrial protein [EP15] and progesterone dependent endometrial protein [PEP]. Studies of the amino acid sequence of these immunologically indistinguishable proteins have demonstrated significant sequence homology with β-lactoglobulins [Julkunen et al., 1990].

Immunolocalization of $\alpha_2$-PEG, PP14 and PEP has been demonstrated in secretory stage glandular epithelium but not the stroma [Sharpe et al., 1993; Joshi et al., 1980, 1986]. Prolactin is synthesized by P-stimulated endometrial stromal cells and immunolocalizes in subpopulations of late secretory stage decidualized stromal cells and in epithelial cells [Maslar and Riddick, 1989; Daly et al., 1983; McRae et a. 1986]. While, these are known, there is no clinical utility for these proteins that would serve as a marker for endometrial receptivity and therefore fertility or infertility.

A great deal of research in the field of fertility therefore involves study of proteins synthesized and secreted by the uterine endometrium. Of additional interest in this area includes a great deal of research pertaining to the disease endometriosis. In particular, the objective of further research is to identify and compare the pattern of in vitro polypeptide synthesis and secretion of normal endometrium with that of the disease endometriosis.

Endometriosis is defined as the ectopic presence of endometrial glands and stroma. Endometriotic tissue is comprised of tissue that is histologically similar yet biochemically and functionally different or out of phase from that of the uterine endometrium.

For example, endometriosis differs from its uterine counterpart in steroid responsiveness and receptor content [Vierikko, et al., 1985; Lessey et al., 1989; Megela et al., 1991] and expression of epidermal growth factor and epidermal growth factor receptor [Megela et al., 1991; Haining et a., 1991]. These altered characteristics, combined with an ectopic location, effect the physiological activity of the endometriotic tissue and thereby alter protein synthesis and secretion by the endometriotic tissue. Deviations in protein synthesis and secretion might be useful in developing unique markers for the nonsurgical diagnosis and management of endometriosis. Unfortunately, limited information is available concerning protein synthesis, secretion, regulation and expression in endometriotic tissue.

Applicant has found dissimilarities in protein synthesis and secretory patterns between eutopic and ectopic uterine tissues (endometriotic implants) using a rat model for endometriosis [Sharpe et al., 1991; Sharpe and Vernon, 1993]. Three groups of endometriotic proteins, synthesized and released in an alternate fashion from uterine proteins, were identified. Two groups of proteins ($M_r$ 40,000 to 55,000; pI 4.0 to 5.2 and $M_r$ 30,000 to 32,000; pI 7.0 to 9.0) were produced by endometriotic implants and not the uteri. The third protein group, ($M_r$ 70,000; pI 5.7), previously identified in uterine explant cultures as progesterone-induced uterine protein-1 [Sharpe et al., 1991], appeared in endometriotic implant cultures 24–48 hours later than in uterine cultures [Sharpe and Vernon, 1993]. The identities, functions, mechanisms of altered protein synthesis and secretion by the ectopic uterine tissues and their correlation to human endometriosis are not known.

Little information in the literature addresses human endometriotic secretory proteins. Isaacson and coworkers [Isaacson et al., 1989] showed that human endometriotic tissues produce and secrete complement component 3 (C3) in an alternate fashion to that of the uterine endometrium. Secretion of C3 into the peritoneal cavity may elicit some of the immunological phenomena observed in patients with endometriosis and be related to the pathophysiology of the disease. However, while C3 may play a role in the pathophysiology of endometriosis, C3 is also produced by other tissues in the body and therefore may not be useful in the development of an endometriosis-specific marker for the disease.

Further identification of biochemical dissimilarities between the uterine endometrium and endometriosis in vitro may enhance our understanding of the mechanism(s) of the pathogenicity of the endometriotic tissue in vivo, potentially leading to the development of improved treatment approaches for endometriosis. Therefore, Applicant desired to identify unique proteins synthesized and secreted by human endometriosis and endometrium in vitro and in vivo.

Protein synthesis and secretion by endometrial and endometriotic tissue explants and isolated endometrial and endometriotic epithelial and stromal cells were examined.

In particular, it is desirable to obtain means and a method for determining endometrial receptivity based on unique proteins synthesized and secreted by human endometrium in vitro and in vivo.

SUMMARY OF THE INVENTION AND ADVANTAGES

In accordance with the present invention, there is provided an isolated and purified glycoprotein and functional analogs thereof characterized by (a) being progesterone induced and estradiol inhibited secretory glycoproteins specifically synthesized and secreted by stromal cells of endometrial origin;

(b) having a molecular weight of 70,000 daltons as determined by two-dimensional sodium dodecyl sulphate polyacrylamide gel electrophoresis (SDS-PAGE);

(c) having an iso-electric point of 5.7; and (d) synthesized by endometrium at the time of fertilization, early embryogenesis, and implantation.

The present invention further provides a method of determining endometrial receptivity by first obtaining a serum or endometrial biopsy sample from a patient and detecting the presence of the above-described glycoprotein.

Finally, the present invention provides an antibody to the purified isolated glycoprotein described above.

BRIEF DESCRIPTION OF THE DRAWINGS

Other advantages of the present invention will be readily appreciated as the same becomes better understood by reference to the following detailed description when considered in connection with the accompanying drawings wherein:

(FIG. 3B) endometrial epithelial cell culture, day 12, cytokeratin mAb (<open arrow>, three-dimensional mound of epithelial cells; <arrowheads>, interconnecting tubular processes; X200); (FIG. 3C) endometrial stromal cell culture, day 8, vimentin mAb (X400); (FIG. 3D) endometriotic epithelial cell culture, day 6, BMA 180/cytokeratin mAbs (X200); (FIG. 3E) endometriotic epithelial cell culture, day 8, cytokeratin mAb (X400); (FIG. 3F) endometriotic stromal cell culture, day 8, vimentin mAb (X400).

DETAILED DESCRIPTION OF THE INVENTION

Figure 1A:
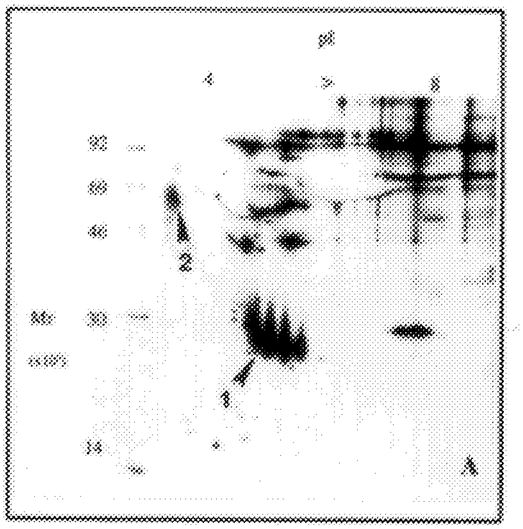
FIGS. 1A–D are representative two-dimensional SDS-PAGE fluorographs of L-[$^{35}$S] methionine-labeled secretory proteins from secretory phase endometrial epithelial cell (FIG. 1A), endometrial stromal cell (FIG. 1B), endometriotic epithelial cell (FIG. 1C), and endometriotic stromal cell (FIG. 1D) culture media.

The present invention generally provides a purified and isolated glycoprotein and functional analogs thereof being characterized by several critical and functional physical characteristics.

Physically, the glycoprotein has been characterized as a N-acetyl linked glycoprotein. As described below in the experimental section, the glycoprotein, named PUP-1, has a molecular weight of 70,000 daltons as determined by two dimensional SDS-PAGE polyacrylamide gel electrophoresis. The glycoprotein has an isoelectric point (pI) of 5.7.

The isolated and purified glycoprotein is secreted as an endometrial product of endometrial stromal cell origin. The glycoprotein is synthesized by the endometrium at the time of fertilization, early embryogenesis and implantation. Additionally, as evidenced below, the PUP-1 glycoprotein is also detected in explant culture media from progesterone treated, but not estrogen treated stromal cells. As further evidenced below, culture media of isolated and purified endometrial stromal cells, but not epithelial cells, from human tissues produce the PUP-1 glycoprotein. Due to the timing of the synthesis of the PUP-1 glycoprotein by the endometrium, and specifically at the time of the reproductive cycle which coincides with fertilization, early embryogenesis, and implantation, PUP-1 protein is clinically useful in the evaluation of endometrial function, differentiation, and implantation as well as in the evaluation of luteal phase physiology.

The N-acetyl linked glycoprotein was isolated and purified by means well-known in the art as described in the experimental section below. The following is an example of the method, exemplifying those methods well-known in the art, for isolating and purifying glycoprotein of the present invention.

Endometrial tissues, obtained by endometrial biopsy, were classified as proliferative (days 4 to 14) or secretory (days 15 to 28) by histological evaluation and according to the date of the last menstrual period of the donor. Use of medication was also recorded. Tissue specimens were transported to the laboratory in saline and dissected free of adnexa.

Endometriotic stromal cells were obtained by enzymatic dissociation and purified by a series of filtrations and sedimentations. Cells were enzymatically dissociated during a 1 hour incubation in Dulbecco's Modified Eagle's Medium/Ham's F-12 (DMEM/Ham's F-12) containing 0.5% collagenase, 0.02% deoxyribonuclease and 2% horse serum in a shaking incubator at 37° C. After 1 hour, the solutions containing the dissociated cells were filtered through an 88 $\mu$m nylon mesh filter. The stromal cell fractions that passed through the 88 $\mu$m filter were purified by gravity sedimentation and a final filtration through a 37 $\mu$m nylon mesh to remove epithelial cells. Cell viability (trypan blue exclusion) and number were evaluated.

Cell fractions were diluted to a density of $1\times10^6$ viable cells/mL and were plated in plastic organ culture dishes for a total of $8\times10^5$ viable cells in a surface area of 176.25 mm$^2$. Cultures were kept in a humidified incubator at 37° C. with 5% $CO_2$. Culture media consisted of DMEM/Ham's F-12 containing 10% heat-inactivated fetal bovine serum for the first 6 days of culture. By day 8 of culture, the cells had achieved approximately 95% confluence and protein studies were initiated. The media was replaced with serum-free minimal essential medium (MEM) containing L-[$^{35}$S] methionine (20 $\mu$Ci/mL) for 24 hours. Incubations were terminated by centrifugation of the media at 3000×RPM for 15 minutes at 4° C. Media containing the de novo synthesized proteins were dialyzed ($M_r$ cut off 6–8000) against 1.0 mM tris, pH 8.2 at 4° C. and lyophilized.

As controls for the isolated stromal cell fractions, endometrial tissue explants (approximately 100 mg wet weight) were incubated in MEM in the presence of L-[$^{35}$S] methionine (20 $\mu$Ci/mL). Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-dimensional polyacrylamide gel electrophoresis (2-D SDS-PAGE) was used to evaluate the de novo synthesized radiolabeled endometrial proteins. Aliquots of lyophilized cell culture and tissue explant media containing $1.5\times10^6$ non-dialyzable copm (6,000 to 8,000 $M_r$ cutoff) were applied to the first dimension isoelectric focusing gels. Molecular weight markers were added to the polyacrylamide (12%) second dimension slab gels. Proteins separated by two dimensional SDS-PAGE were transferred to nitrocellulose membranes at one amp constant current for one hour using the Hoeffer Transphor® Blot System and visualized by fluorography. The BioRad 2D Analyst software with BioRad Model 620 densitometer was used to create digital contour maps of images on the fluorographs made from the two-dimensional SDS-PAGE protein separations. Computer generated peak reports were used for qualitative comparison of proteins form the contour maps.

By functional analogs, it is meant an analog will be generally at least 70% homologous over any portion that is functionally relevant. In more preferred embodiments the homology will be at least 80% and can approach 95% homology to the glycoprotein. The amino acid sequence of an analog may differ from that of the glycoprotein of the present invention when at least one residue is deleted, inserted or substituted. Differences in glycosylation can provide analogs. The molecular weight of a glycoprotein can vary between the analog and the present invention due to carbohydrate differences.

The term "progesterone induced and estradiol inhibited secretary glycoprotein" is used to indicate that at least in culture, PUP-1 is isolated and purified from endometrial stromal cells, but not epithelial cells by the addition of progesterone to the media for inducement and addition of estradiol to the media for inhibition.

As evidenced below, the purified isolated glycoprotein can be detected in endometrial biopsy specimens. According, since Applicant has provided experimental evidence of the synthesis, secretion and localization of PUP-1, specifically during the luteal phase, the time of endometrium receptivity, the present invention can provide a method of determining endometrial receptivity. Generally, the method includes the steps of first obtaining a serum or endometrial sample by methods well-known in the art. Serum may be collected by venipuncture into a red top tube. Endometrial tissue can be obtained using a Pipelle™ (Unimar, Wilton, Conn.) endometrial suction curette. Tissues are then transported to the laboratory in saline. The method would then include the quantitative detection of the presence of the glycoprotein PUP-1.

The detection of the glycoprotein can be accomplished by various methods. The experimental data below demonstrate immunochemical localization of the PUP-1 protein. Immunochemical methods for such a detection are well-known in the art. The glycoprotein may be detected in formalin fixed, paraffin embedded tissues by immunohistochemistry using the avidin-biotin peroxidase method [Sharpe et al., 1994]. It is also advantageous to immunohistochemically stain the tissues sections for cytokeratin and prolactin to identify the specific cell populations. (See *Basic and Clinical Immunology* (Stites and Terr, eds., Seventh Edition) Appleton & Lange, Norwalk, Conn. (1991), pp 245–251 for a general discussion of immunohistochemical techniques). The glycoprotein may also be immunohistochemically detected in sera or culture media of SDS-PAGE separated glycoproteins by Western blot analysis, a technology well known to those skilled in the art as described generally in Harlow and Lane, *Antibodies: A Laboratory Manual*, Cold Spring Harbor Laboratory, Cold Spring Harbor, N.Y., 1988; pp 475–501 and as used by the Applicant [Sharpe et al., 1993].

Applicant provides herein below immunochemical localization methods of the PUP-1 glycoprotein. To achieve the results, Applicant has developed polyclonal antibody made from de novo synthesized and purified PUP-1. This antibody is demonstrated to have clinical utility for the detection of the PUP-1.

Antibodies may be either monoclonal or polyclonal, in the preferred embodiment they are polyclonal. Antibodies may be generated from isolated, partially purified glycoprotein or, alternatively, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and as is described hereinbelow in the Examples for "off-blot" generation of antibody.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}$C and iodination. In a preferred embodiment, the avidin-biotin peroxidase system is used.

As evidenced by the studies below, PUP-1 is specifically a product of secretory phase endometrial stromal cells and localizes in the decidua and trophoblast throughout gestation. Accordingly, PUP-1 can be clinically useful as a diagnostic marker for progesterone dependent endometrial/placenta functions. Specifically, the experimental evidence below shows the isolated glycoprotein can be useful in the method to determine endometrial receptivity, the presence of the glycoprotein indicating endometrial receptivity.

The determination of endometrial receptivity utilizing a biochemical marker is critical in combination with morphological analysis of the cells. This is because although a biopsy may determine structural indications of receptivity, this does not necessarily mean that the endometrial cells are biochemically and functionally in phase. Preferably, use of the purified isolated glycoprotein marker from biopsy or serum samples in combination with structural analysis will provide critical information with regard to the functional receptivity of the endometrium for implantation. This information in combination with other fertility factors is extremely useful in the analysis of fertility. Finally, such information can provide necessary information critical to therapy if needed.

The above discussion provides a factual basis for the use of PUP-1 glycoprotein and functional analogs thereof as markers for endometrial receptivity. The methods used with and the utility of the present invention can be shown by the following examples.

EXAMPLES

EXAMPLE 1

Isolation and Characterization of Glycoprotein

MATERIALS AND METHODS

Endometrial and Endometriotic Tissue

Human tissues were obtained from randomly selected, informed volunteer patients routinely presenting to the physicians in the Department of Obstetrics and Gynecology at the University of Missouri Medical School as approved by the Institutional Review Board. Patients presented for a variety of routine diagnostic and therapeutic examinations including diagnosis of endometrial function, endometriosis, tubal ligation for sterilization, routine gynecological care and gamete intrafallopian transfer.

Endometrial tissue was obtained using a Pipelle™ (Unimar, Wilton, Conn.) endometrial suction curette. Endometriotic tissue was obtained at the time of laparoscopic examination. Peritoneal endometriotic implants, including red petechia and reddish-brown lesions, were elevated with biopsy forceps and the area circumscribed by either laser or sharp dissection. Powder-burn implants and cystic ovarian endometriosis were excluded from the study. Vernon and associates have shown [Vernon et al., 1986] that the metabolic activity of the reddish implants appears to be greatest when compared with the brown or black lesions. Ovarian endometriosis was excluded to eliminate the possibility of "contaminating" ovarian cells in the cell culture experiments. The date of the patients last menstrual period and use of any medication were also recorded. Endometrial and endometriotic tissues were classified as proliferative (days 4 to 14) or secretory (days 15 to 28) according to the date of their last menstrual period. Endometrial dating and the presence of endometriosis were confirmed by histological evaluation by the Pathology Department at the University of Missouri. Tissue specimens were transported to the laboratory in saline and, using a dissecting microscope, dissected free of adnexa. Epithelial and stromal cell cultures plus tissue explant cultures were processed as described below.

Epithelial and Stromal Cell Isolation And Purification

Epithelial and stromal cells were obtained by enzymatic dissociation and a series of filtrations and sedimentations according to the protocol of Osteen et al. [1989] with modifications described by Sharpe et al. [1992]. Briefly, cells were enzymatically dissociated from endometrial and endometriotic tissues during a 1 hour incubation in phenol-red free Dulbecco's Modified Eagle's Medium/Ham's F-12 (DMEM/Ham's F-12; Sigma Chemical Co., St. Louis, Mo.) containing 0.5% collagenase (Clostridium histolyticum, catalogue number 840–7018IH), 0.02% deoxyribonuclease (DNase, Sigma Chemical Co., St. Louis, Mo.) and 2% horse serum (Vector Laboratories, Burlingame, Calif.) in a shaking incubator at 37° C. After 1 hour, the solutions containing the dissociated cells were filtered through an 88 $\mu$m nylon mesh filter. The stromal cell fractions that passed through the 88 $\mu$m filter were further purified by gravity sedimentation and a final filtration through a 37 $\mu$m nylon mesh to remove remaining epithelial cells. Cell viability (0.04% trypan blue exclusion test) and number (Makler Counting Chamber, T. S. Scientific, Perkasie, Pa.) were evaluated in aliquots of the cells.

The epithelial cell fractions retained by the filters in the initial filtration step were subjected to a second enzymatic digestion for 30 to 45 minutes or until cell clumps were dispersed. The dispersed epithelial cell fractions were further purified by gravity sedimentation and selective attachment procedures [Sharpe et al., 1992]. Cell number and viability were evaluated as described for the stromal cell fractions.

Isolation and purification of epithelial and stromal cells yielded an average of $2.1\times10^4$ viable epithelial cells and $2.6\times10^5$ viable stromal cells per mg of tissue. Both stromal and epithelial cell fractions were diluted to a density of $1\times10^6$ viable cells/mL. Stromal cell suspensions (0.8 mL each) were plated in plastic organ culture dishes (Falcon 3037, Falcon Plastics, Oxnard, Calif.) for a total of $8\times10^5$ viable cells in a surface area of 176.25 $mm^2$. Epithelial cell suspensions (0.4 mL) were plated in Millicelle CM culture inserts (Millipore, Bedford, Mass.) coated with 0.2 mL of the extracellular matrix Matrigel® (non-diluted; Collaborative Research Inc., Bedford, Mass.) providing a total of $4\times10^5$ viable cells in a surface area of 78.50 $mm^2$. Aliquots of the epithelial cell suspensions were also plated on plastic cultureware for immunocytochemical analysis as Matrigel® often created an unacceptable background in the staining process. Other than the elimination of the high background staining, the results of the immunostaining did not vary between the two culture types (matrix vs plastic). All cultures were kept in a humidified incubator at 37° C. with 5% $CO_2$. Culture media consisted of phenol-red free DMEM/Ham's F-12 containing 10% heat-inactivated fetal bovine sera (GIBCO/BRL, Grand Island, N.Y.) for the first 6 days of culture. By day 8 of culture, the cells had achieved approximately 95% confluence and protein studies were initiated. The cultures were rinsed 3 times with phosphate buffered saline and the media was replaced with serum-free minimal essential medium (MEM; Gibco/BRL, Grand Island, N.Y.) containing L-[$^{35}$S] methionine (20 $\mu$Ci/mL; Du Pont New England Nuclear, Boston, Mass.) for 24 hours. Incubations were terminated by centrifugation of the media at 3000×RPM for 15 minutes at 4° C. Media containing the de novo synthesized proteins were dialyzed ($M_r$ cut off 6–8000) against 1.0 mM tris (hydroxymethyl) aminomethane HCl, pH 8.2 at 4° C. and lyophilized.

Cell morphology was assessed and photomicrographed at plating (day 0) and days 4, 6, 8 and 12 at ×100, ×200 and ×400 magnification using a Nikon Diaphon™ inverted phase contrast microscope (Nikon, Inc., Garden City, N.Y.) with a Hoffman Modulation Contrast System (Modulation Optics, Inc. Greenvale, N.Y.). Cells were evaluated before and after immunostaining and with a hematoxylin counterstain.

A variety of intermediate filament protein, glycoprotein and secretory protein markers were used to assess the various cell types present in the endometrial and endometriotic cell cultures. Attempts were made to identify a marker which would distinguish between endometriotic cells and peritoneal cells. Murine monoclonal antibodies (MAbs) against: cytokeratins 8, 18 and 19 (for epithelial cells; Biodesign clone NCL-5D3; Kennebunkport, Me.); vimentin (for stromal cells; Boehringer Mannheim clone V9; Indianapolis, Ind.); a human epithelial cell marker directed against a 200 kilo-Dalton glycoprotein, BMA 180 (also known as BW 495/36; for endometrial/endometriotic epithelial cells; Behringwerke AG, Marburg, Germany); and for pregnancy-associated endometrial $\alpha_2$-globulin ($\alpha_2$-PEG; C6H11; for secretory phase endometrial epithelial cells) were used to assess the cells at plating and on days 4, 6, 8 and 12. The $\alpha_2$-PEG (C6H11; 1:100) MAb used as a marker of secretory phase epithelial cell purification and also as an indicator of physiological function in vitro by Western blot analysis of explant culture media separated by 2D-PAGE. Single and double labeling immunocytochemical techniques were performed using the Vectastain® ABC (avidin:biotin complex peroxidase procedure) and ABC-AP (avidin:biotin complex alkaline phosphatase procedure) Kits (Vector Laboratories) as per manufacturer's instructions. Peroxidase activity was demonstrated by incubation with 3,3'-diaminobenzidine substrate yielding a brown intracellular precipitate which confirmed peroxidase staining. Alkaline phosphatase activity was demonstrated with the Vectastain® Alkaline Phosphatase Substrate Kit I-Vector Red yielding a pinkish-red stain which confirmed alkaline phosphatase activity. Cells were counterstained with hematoxylin. Cells incubated with phosphate buffered saline substituted in place of primary antibody were included as negative controls in all immunostaining procedures. Using inverted phase contrast microscopy, multiple fields (×200) per cell type were evaluated for the percent of reactive cells.

Tissue Explant Culture

As controls for the isolated epithelial and stromal cell fractions, endometrial and endometriotic tissue explants (approximately 100 mg wet weight) were incubated in MEM in the presence of L-[$^{35}$S] methionine (20 $\mu$Ci/mL) as previously used by Sharpe et al. [Sharpe et al., 1991] and Sharpe and Vernon [Sharpe and Vernon, 1993]. Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-Dimensional Electrophoresis and Western Blot Analysis

Two-dimensional polyacrylamide gel electrophoresis (2-D SDS-PAGE) was performed as previously employed by Sharpe et al. [1993] and Sharpe and Vernon [1993]. To evaluate the de novo synthesized radiolabeled proteins, aliquots of lyophilized cell culture and tissue explant media containing 1.5×10$^6$ non-dialyzable cpm (6,000 to 8,000 $M_r$ cutoff) were applied to the first dimension isoelectric focusing gels. Molecular weight markers (Pharmacia LKB Biotechnology, Inc. Piscataway, N.J.) were added to the polyacrylamide (12%) second dimension slab gels. Proteins separated by two dimensional SDS-PAGE were transferred to nitrocellulose membranes (Schleicher and Schuell, Keene, N.H.) at one amp constant current for one hour using the Hoeffer Transphor® Blot System (Hoeffer Scientific, San Francisco, Calif.) and visualized by fluorography. The BioRad 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps. Due to the overload of protein in some of the two-dimensional SDS-PAGE gels and possible loss of resolution following transfer of the proteins to nitrocellulose prior to autoradiography, only protein groups representing at least 10% of the integrated intensity were evaluated. Quantitative comparisons between patients or between tissue/cell cultures were not made.

RESULTS

Endometrial and Endometriotic Tissue Specimens

Twenty-nine specimens were evaluated (Table 1). Twenty-two of the specimens were obtained from women with histories of regular menses. Seven additional specimens were obtained from women with atypical or absent menstrual cycles. Specimens ranged from 29 mg to over 4 g in weight. Up to 100 mg of tissue was used for explant culture and remaining tissue was enzymatically dissociated for the cell culture experiments.

TABLE 1

Source of Tissue Specimens

| Tissue Source | No. of specimens |
|---|---|
| Regular menses | |
| Matched endometrial/endometriosis biopsy | 16 |
| Endometrial biopsy only | 2 |
| Endometriosis biopsy only | 4 |
| Total | 22 |
| Atypical of absent menses | |
| Endometrial biopsy, irregular bleeding | 1 |
| Endometrial biopsy, irregular bleeding-MPA | 1 |
| Endometrial biopsy, perimenopausal | 1 |
| Endometriosis biopsy, danazol | 2 |
| Endometriosis biopsy, prior hysterectomy | 2 |
| Total | 7 |

Protein Synthesis and Secretion

Patterns of proteins synthesis and secretion made from the isolated endometrial and endometriotic epithelial and stromal cell culture media from women with regular menses are shown in FIGS. 1A–1D. Of the hundreds of proteins visualized on the two-dimensional SDS-PAGE fluorographs, five major groups of unique proteins, unique to either endometrial or endometriotic cultures and each representing at least 10% or more of the total integrated intensity of the radioactivity, were resolved and assigned to one of five groups. The proteins assigned to endometrial protein group I ($M_r$ 25,000 to 27,000; pI 4.5 to 5.5) and endometrial protein group II ($M_r$ 68,000 to 72,000; pI 3.0 to 3.2) were synthesized by secretory, but not proliferative phase, endometrial epithelial cells (FIG. 1A). Endometrial protein groups I and II were not found in the culture media of endometrial stromal cells (FIG. 1B), endometriotic epithelial cells (FIG. 1C) or endometriotic stromal cells (FIG. 1D) regardless of the stage of the reproductive cycle.

Figure 1B:
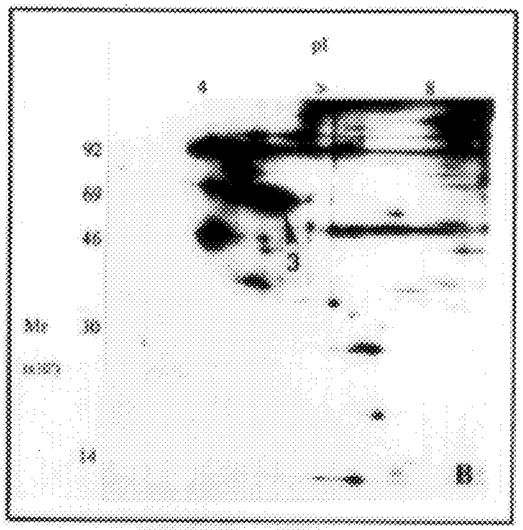
Figure 1C:
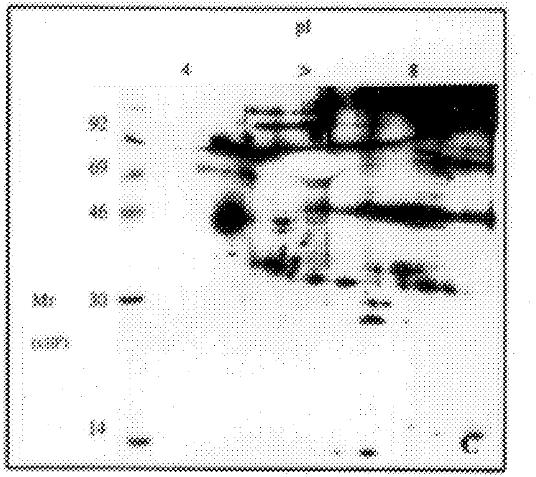
Figure 1D:
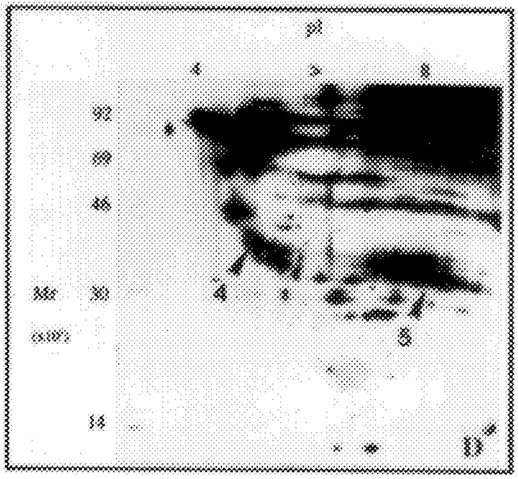

Endometrial protein group III ($M_r$ 70,000; pI 5.7) was synthesized and secreted by secretory, but not proliferative phase, endometrial stromal cells (FIG. 1B). Endometrial protein group III was also synthesized and secreted by two of seven proliferative endometriotic specimens (not shown) but none of the secretory phase endometriotic specimens tested (FIG. 1C and 1D). Thus, the proliferative phase release of endometrial protein group III by endometriotic specimens was "out of Phase" with that of the secretory phase uterine endometrial release of endometrial protein group III.

Endometriosis protein groups I ($M_r$ 40,000 to 55,000; pI 4.0 to 5.2) and II ($M_r$ 30,000 to 32,000; pI 7.0 to 9.0) were produced by endometriotic stromal cells (FIG. 1B) independent of menstrual cycle stage. Endometriosis protein groups I (ENDO I) and II (ENDO II) were not synthesized by endometrial epithelial cells (FIG. 1A), endometrial stromal cells (FIG. 1B) or endometriotic epithelial cells (FIG. 1C) regardless of menstrual cycle stage.

Figure 2A:
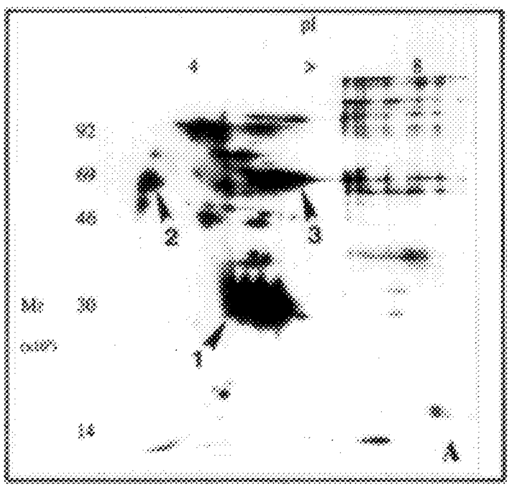
FIGS. 2A–B are representative two dimensional SDS-PAGE fluorographs of L-[$^{35}$S] methionine-labeled secretory proteins from secretory phase endometrial epithelial cell (FIG. 2A), and endometriotic (FIG. 2B) explant culture media.
Figure 2B:
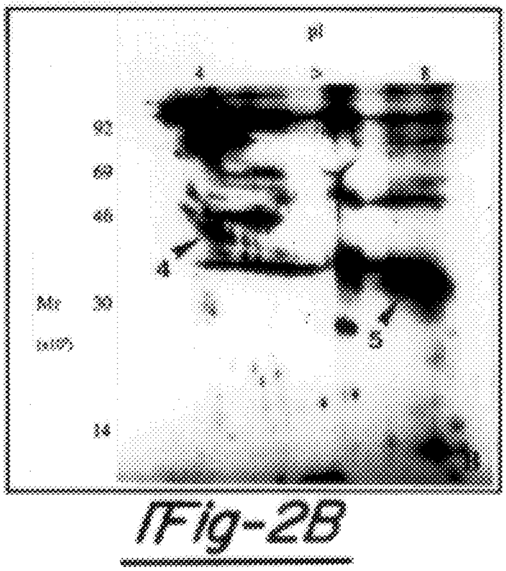

The patterns of synthesis and secretion of the five protein groups visualized and evaluated in the cell culture media were identical to those evaluated in the explant culture media. Endometrial protein groups I, II and III were secretory phase endometrial explant products (FIG. 2A). Endometrial protein groups I and II were not found in endometriotic explant cultures from women with regular menses regardless of the phase of the menstrual cycle (FIG. 2B) while endometrial protein group III was synthesized and secreted by two of seven proliferative phase endometriotic specimens. Also paralleling the cell culture results, endometriosis protein groups I and II were found in endometriotic explant culture media (FIG. 2B) but not endometrial explant culture media (FIG. 2A) regardless of the menstrual cycle stage. Overall, no difference was noted in the pattern of endometrial protein synthesis and secretion between specimens from patients with and without endometriosis.

Western blot analysis of culture media showed that only endometrial protein group I displayed immunoreactivity with the MAb raised against human $\alpha_2$-PEG. No immunoreactivity for $\alpha_2$-PEG was detected in the endometriotic culture media by Western blot analysis. This parallels the lack of $\alpha_2$-PEG immunoreactivity found in the endometriotic epithelial cells as described below.

A limited number of specimens were cultured from women reporting atypical or absent menses. Proliferative endometrium from a patient with irregular uterine bleeding (no current medication) aberrantly synthesized and secreted secretory phase endometrial protein groups II and III and endometriosis protein groups I and II. This was the only case in which endometrial protein groups II and III were produced by a proliferative endometrial specimen and the only case in which the endometriosis protein groups I and II were produced by an endometrial biopsy specimen in this study. Subsequent histological diagnosis revealed adenomyosis.

Proliferative endometrium from a patient taking medroxyprogesterone acetate (MPA) for irregular uterine bleeding more closely resembled that observed for a proliferative endometrium from patients with regular menses. That is, the proliferative endometrium from the MPA patient did not synthesize the secretory phase endometrial protein group II nor the endometriosis protein groups I and II but did, however, aberrantly synthesize and secrete endometrial protein group III, suggesting that this protein group may be modulated by progesterone (P). Secretory endometrium was obtained from a perimenopausal patient. This specimen lacked the ability to produce endometrial protein groups I and II but retained the ability to produce endometrial protein group III. This perimenopausal specimen did not synthesize and secrete endometriosis protein groups I or II.

The pattern of protein synthesis and secretion was also evaluated from endometriotic tissue specimens obtained from patients taking danazol for endometriosis (n=2) and patients who had undergone a prior hysterectomy (n=2). None of these endometriotic specimens produced the endometrial protein groups I, II or III. However, despite the fact that these women had received therapy for endometriosis, half (n=2/4) of these endometriotic specimens continued to synthesize and secrete endometriosis protein groups I and II.

Epithelial and Stromal Cell Culture

Figure 3A:
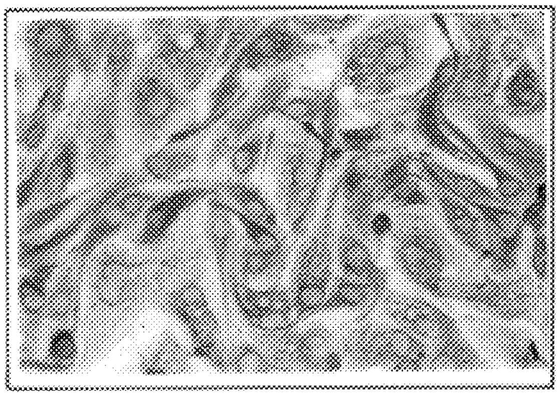
FIGS. 3A–F are photomicrographs of primary cultures of separated epithelial and stromal cells from endometrial and endometriotic biopsy specimens wherein (FIG. 3A) endometrial epithelial cell culture, day 8, cytokeratin mAb (X400)
Figure 3B:
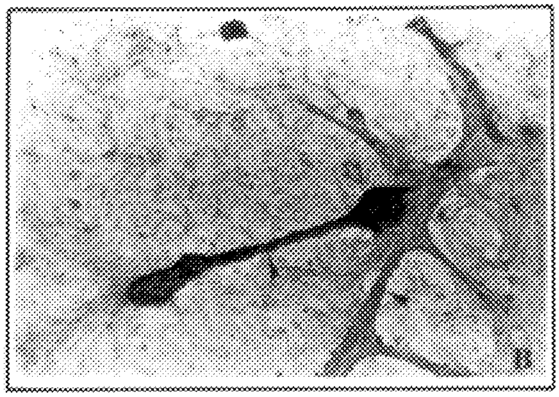
Figure 3C:

Morphologically, by day 8 of culture, endometrial epithelial cells cultured on the extracellular matrices plated on a semipermeable membrane appeared as homogeneous populations of tadpole-shaped cells with prominent, off-centered nuclei and whorling cell-cell processes that wrapped around adjacent cells (FIG. 3A). By day 12 of culture, the monolayers of endometrial epithelial cells formed three-dimensional mounds of cells which appeared interconnected by tubular processes resembling glandular-like structures (FIG. 3B). Endometrial stromal cells displayed a homologous, cobblestone mosaic-like, single cell monolayer pattern. The endometrial stromal cells had centrally located nuclei, distinct cytoplasmic borders which did not overlap and did not demonstrate cell-cell processes throughout the experiment (FIG. 3C).

Figure 3D:
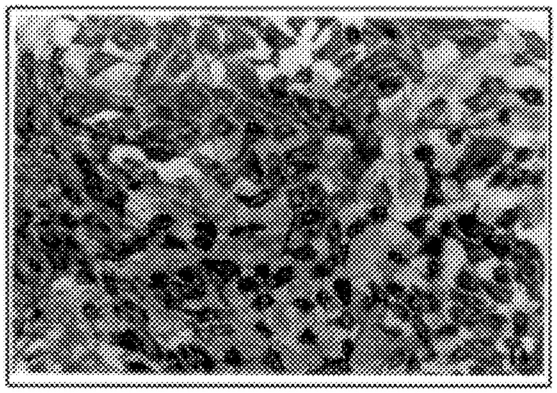
Figure 3E:
Figure 3F:
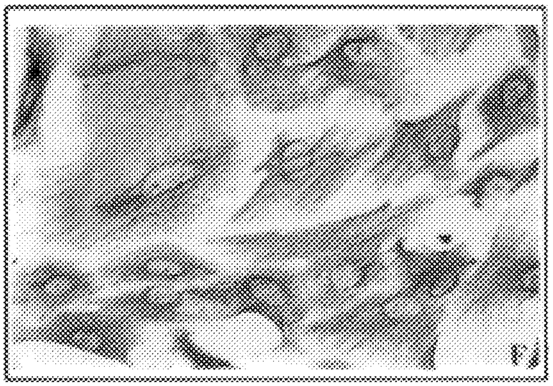

Cell fractions isolated from the endometriotic specimens contained morphologically and immunocytochemically distinct populations of cells. Subconfluent endometriotic epithelial cell fractions observed on days 4 and 6 (FIG. 3D) contained two layers of cells as determined by inverted phase contrast microscopy. An upper layer of cells with multiple long, ultrafine cell-cell processes appeared to be precursors to the tadpole-shaped endometriotic epithelial cells. A sublayer of larger, polymorphous-shaped cells displayed a continuum of cell morphology ranging from polygonal to elongated spindle-like shapes which were not observed in any of the endometrial epithelial cell cultures (FIG. 3E). By day 8 of culture, the surface layer had overgrown the sublayer so that the cells of the endometriotic epithelial cell cultures appeared tadpole-shaped and morphologically similar to the endometrial epithelial cell cultures (FIG. 3A). The endometriotic stromal cell fractions (FIG. 3F) appeared as single cell monolayers with cells which had centrally located nuclei, distinct cytoplasmic borders and no obvious cell-cell processes much like the morphology of the endometrial stromal cells (FIG. 3C).

The results of the immunocytochemical staining of the cells did not differ between the day of plating and days 4, 6, 8 and 12 and are presented in Table 2. Endometrial epithelial cells, especially those cells involved in formation of the epithelial cell mounds and tubular gland-like structures, displayed strong immunoreactivity with the cytokeratin and BMA 180 MAbs. Few (<3%) of the cells in the endometrial epithelial cells were decorated with the vimentin MAb suggesting limited stromal cell contamination of the epithelial cell cultures. Secretory, but not proliferative phase, endometrial epithelial cells were also decorated with the $\alpha_2$-PEG MAb (C6H11). The surface layer of tadpole-shaped endometriotic epithelial cells displayed similar immunostaining characteristics to the endometrial epithelial cells for cytokeratin, vimentin and BMA 180, but only the endometrial epithelial cells were decorated with the MAb raised against human $\alpha_2$-PEG (Table 2).

The surface and sublayers of the endometriotic epithelial cell cultures displayed different patterns of immunostaining (Table 2). While both layers stained positively for cytokeratin and negatively for $\alpha_2$-PEG, double antibody staining techniques revealed that only the upper layer of tadpole-shaped cells was decorated with the BMA 180 MAb (FIG. 3D) and only the polymorphous sublayer was decorated with vimentin.

Endometrial and endometriotic stromal cells were both decorated with the vimentin MAb and did not display immunoreactivity with the epithelial cell markers BMA 180 and $\alpha_2$-PEG. However, only the endometriotic stromal cells were decorated with the cytokeratin MAb.

Example 1 has identified distinct differences in the synthesis and release of proteins by human endometriosis and uterine endometrium in culture. Unique, endometrial secretory proteins and unique endometriosis-specific secretory proteins could be of hallmark importance in the development of novel diagnostic, prognostic and therapeutic methods for the management of endometrial receptivity and the disease endometriosis, possibly reducing the need for surgical intervention in the diagnosis and treatment of related disorders. Furthermore, understanding biochemical dissimilarities between endometrium and endometriosis may enhance our knowledge of endometrial receptivity and associated spontaneous abortion and/or enhance our knowledge of the etiology and/or pathophysiology of the disease endometriosis potentially leading to new treatment approaches related reproductive dysfunction.

As endometriosis protein groups I and II ($M_r$ 40,000 to 55,000; pI 4.0 to 5.2 and $M_r$ 30,000 to 32,000; pI 7.0 to 9.0, respectively) were synthesized and secreted by endometriotic cultures but not endometrial cultures from women with regular menstrual cycles, they are markers for endometriosis, as set forth in Applicants' copending application U.S. Ser. No. 328,451, filed Oct. 25, 1994, assigned to the same assignee and incorporated herein by reference. In addition to their presence in all endometriosis explant culture and endometriosis stromal cell culture media from patients who were not receiving treatment for the disease, endometriosis protein groups I and II were also found in half of the endometriosis cultures derived from women who either had received danazol or had undergone a prior hysterectomy for endometriosis. The continued synthesis and secretion of endometriosis protein groups I and II by endometriotic tissues from women who had undergone these therapies may be one possible explanation for treatment failures. On only one occasion were the endometriosis proteins observed in endometrial culture media. Curiously, this endometrial biopsy was obtained from a women with irregular uterine bleeding who was subsequently diagnosed with adenomyosis. Evaluation of additional numbers of biopsy specimens from patients with irregular menstrual cycles or who have undergone some form of endometriosis therapy are needed.

Example 1 has also identified three groups of secretory phase endometrial proteins whose synthesis and secretion by endometriosis is absent or altered. Endometrial protein group I ($M_r$ 25,000 to 27,000; pI 4.5 to 5.5) was identified as the secretory phase endometrial protein $\alpha_2$-PEG on the basis of its unique appearance in the secretory phase of the menstrual cycle, by electrophoretic mobility in two-dimensional SDS-PAGE, by Western blot analysis of endometrial culture media and by immunocytochemistry with cell cultures using the MAb C6H11 raised against human $\alpha_2$-PEG [Bell SC, 1986]. Using these same criteria, $\alpha_2$-PEG was not detected in the endometriotic explant or endometriotic cell culture media nor by immunostaining of the endometriotic cell cultures regardless of the day of the reproductive cycle at which the specimens were obtained.

In recent years, $\alpha_2$-PEG has received considerable attention, appearing in the literature under various names including progesterone-associated endometrial protein (PEP), placental protein 14 (PP14) and alpha-uterine protein (AUP) [Seppala et al., 1992]. Telimaa and coworkers [Telimaa et al., 1989] found elevated serum levels of PP14 in patients with advanced endometriosis and suggested that the endometriotic lesions were contributing to the elevated serum levels of PP14. Cornillie and coworkers [Cornillie et al., 1991] noted that 36% of all endometriotic lesions studied displayed PP14 immunoreactivity yet as few as 6% of the lesions displayed strong PP14 immunostaining. Low levels or the lack of detection of PP14/$\alpha_2$-PEG in endometriotic tissues or culture media, respectively, may be related to methodology.

Cornillie and coworkers [Cornillie et al., 1991] evaluated PP 14 expression in paraffin fixed tissues while we evaluated $\alpha_2$-PEG of culture media and cultured cells. Alternatively, tissues or cells may require the addition of P to the culture media prior to the synthesis and secretion of $\alpha_2$-PEG. Yet, the relatively low number of PP14 immunoreactive endometriotic lesions detected in [Cornillie et al., 1991] studies combined with our lack of detection of $\alpha_2$-PEG in the endometriosis explant or cell culture media or cultured cells also suggests that the elevated serum levels of this protein in patients with endometriosis may be originating from another source. Recent studies have indeed shown that this protein may also be synthesized and secreted by the ovary [Critchley et al., 1992; Riitten L. 1992]. However, due to considerable overlap in PP14 measurements in women with and without endometriosis, measurement of PP14 is not predicted to become a diagnostic or prognostic test for endometriosis [Seppala et al., 1992].

Little is known about endometrial protein group II other than the molecular size and isoelectric point as determined by electrophoretic mobility in two-dimensional SDS-PAGE ($M_r$ 68–72,000; pI 3.0–3.2). Endometrial protein group II appears to be unique to secretory phase endometrial explant and epithelial cell cultures and may, as such, be useful as a marker for endometrial function or dysfunctions such as luteal phase defect. Very limited data (n=2) suggests that medroxyprogesterone acetate therapy may also modulate the synthesis and secretion of endometrial protein group II. This observation remains to be confirmed. Thus, both endometrial protein groups I and II may be useful in monitoring therapeutic modalities for progesterone-modulated endometrial function.

Endometrial protein group III ($M_r$ 70,000; pI 5.7) was a major product of secretory, but not proliferative, endometrial explant and stromal cell cultures. Endometrial protein group III was also found in a proliferative phase endometrial explant culture derived from a patient who was taking MPA for irregular uterine bleeding. These observations suggests that endometrial protein group III is P modulated and may play a role in progesterone-dependent uterine function. The synchronous, proliferative phase synthesis and release of endometrial protein group III by the endometriotic lesion as compared to secretory phase uterine production suggests that the endometriotic tissue responds to stimuli in an altered fashion. The release of an endometrial protein by the endometriotic lesion at an inappropriate time of the menstrual cycle might either enhance or be detrimental to normal physiological events. An additional interesting observation is the presence of endometrial protein group III but not endometrial protein groups I and II in the culture media of a secretory phase specimen obtained from a perimenopausal women. The lack of secretion of endometrial protein group I in perimenopausal patients agrees with earlier reports of the lack of PP14 mRNA expression in postmenopausal endometrium [Julkunen et al., 1988]. Altered secretory phase synthesis and secretion of endometrial proteins around the time of the menopause requires further investigation.

Endometrial protein group III may be a homologue to rat progesterone-induced uterine protein-1. Similarities including co-migration in two-dimensional SDS-PAGE, synthesis and secretion under conditions of elevated serum P [Sharpe et al., 1991], and synchronous synthesis and secretion by endometriotic tissues [Sharpe and Vernon, 1993] suggest that endometrial protein group III may be the human homologue for the rat progesterone-induced uterine protein-1.

The distinct differences in endometriosis and endometrial protein synthesis and secretion observed add to the growing list of biochemical dissimilarities which exists between these two tissues.

Despite careful attempts of dissection, minimal amounts of peritoneal tissue remained with the endometriotic lesions as they were placed into tissue explant culture or processed for cell culture. This peritoneal tissue may have been the source of the polymorphous cells of the endometriotic epithelial cell cultures. The polymorphous cells observed in this Example and proliferating peritoneal mesothelial and/or subserosal cells [Bolen et al., 1986] display similar morphologies and both co-express vimentin and lower-molecular weight cytokeratins. Furthermore, the lack of $\alpha_2$-PEG and BMA 180 immunoreactivity suggests that the polymorphous cells are not of endometrial origin. Kruitwagen and others [Kruitwagen et al., 1991] have reported that endometriotic epithelial cells but not peritoneal mesothelial cells are immunoreactive with the BMA 180 MAb. The endometriotic stromal cell cultures may also have contained cells of peritoneal origin which co-expressed cytokeratin and vimentin giving the impression that the endometriotic stromal cells expressed cytokeratin. Alternatively, the presence of peritoneal cells may have altered the intermediate filament expression of the endometriotic stromal cells. Subserosal peritoneal cells have been shown to demonstrate striking changes in intermediate filament expression in response to infiltrating tumors [Bolen, et al., 1986]. An antibody which distinguishes between endometriotic stromal and peritoneal cells is not presently available; an antibody developed for endometrial protein group III might be useful as such a marker. Nonetheless, in this in vitro cell culture model, much like in vivo, endometriotic epithelial and stromal cells juxtapose peritoneal mesothelial and/or subserosal cells which might elicit or contribute to deviations in protein synthesis and secretion.

TABLE 2

Immunocytochemical Staining of Isolated Populations of Endometrial and Endometriotic Epithelial and Stromal Cell Fractions

| | Epithelial cell fraction | | | Stromal cell fraction | |
|---|---|---|---|---|---|
| | Endometrial tissue Tadpole | Endometriotic tissue Tadpole | Endometriotic tissue Polymorph | Endometrial tissue Cobblestone | Endometriotic tissue Cobblestone |
| Cytokeratin | +* | + | + | o | + |
| Vimentin | o† | o | + | + | + |
| BMA 180 | + | + | o | o | o |
| $\alpha_2$-PEG | s‡ | o | o | o | o |

*+, Immunoreactivity detected during proliferative and secretory phases of the menstrual cycle.
†o, no immunoreactivity detected in either phase of the menstrual cycle.
‡s, immunoreactivity detected only in secretory phase of the menstrual cycle.

EXAMPLE 2

The Synthesis And Release Of Endometriotic Secretory Proteins Differs From That Of The Uterine Endometrium To access the ability of the endometriotic lesion to synthesize and secrete endometrial proteins, in vitro protein production by uterine endometrium and endometriotic tissues was examined. Matched biopsy specimens of uterine and endometriotic tissues were collected at the time of laparoscopic diagnosis for endometriosis. Menstrual cycle stage (n=5 follicular [cycle day 4–12] and 7 secretory [cycle day 19–27]) and the presence of endometriosis was documented histologically. Tissue explants plus isolated, purified, 90% confluent epithelial and stromal cells were cultured for 24 hours in minimal essential medium containing $^{35}$S-methionine (100 $\mu$Ci/ml). Tissue and cell culture media containing the de novo synthesized proteins was centrifuged, dialyzed and lyophilized and the proteins separated and visualized by two-dimensional gel electrophoresis and fluorography. Although hundreds of similar proteins were produced by both tissue types, two major groups of proteins, Groups I and II, were found to be unique secretory products of the epithelial cells of the secretory uterine endometrium and were not secreted by the endometriotic tissue regardless of the cycle day. Secretion of Group III was augmented in stromal cells of the uterine cultures as compared to the endometriotic cultures while secretion of Group IV was enhanced in the stromal cells of the endometriotic cultures as compared to those of the uteri.

| Group | Mr | pI | Tissue | Cells |
|---|---|---|---|---|
| I | 25–27,000 | 4.5–5.5 | Secretory endometrium (d 19–23) | Epithelial |
| II | 72–85,000 | 3.0–3.2 | Secretory endometrium only | Epithelial |
| III | 70,000 | 5.7 | Uterine > Endometriosis | Stromal |
| IV | 30–32,000 | 6.5–8.0 | Endometriosis > Uterine | Stromal |

The two-dimensional electrophoretic mobility and distinctive secretory has, epithelial cell secretory pattern suggest that Group I is β-lactoglobulin (pregnancy associated endometrial globulin, $\alpha_2$-PEG), a major secretory protein of the glandular epithelium of the human endometrium. Group III co-migrates with the rat progesterone-induced uterine protein-1 (PUP-1, also of stromal origin) and may be the human homologue for PUP-1. The highly acid Group II and basic Group IV have not been previously identified. Overall, the altered patterns of protein synthesis and secretion offer additional insight into the biochemical differences which exist between the uterine endometrium and endometriotic lesion.

EXAMPLE 3

Immunolocalization Of PUP-1 In Human Endometrium, And Endometrial Epithelial And Stromal Cell Cultures

MATERIALS AND METHODS

Supplies

Pipelle™ endometrial suction curettes were obtained from Unimar (Wilton, Conn.). 10% neutral buffered formalin was purchased from Fisher Scientific (St. Louis, Mo.). Millicelle CM culture inserts were obtained from Millipore (Bedford, Mass.) and plastic organ culture dishes (Falcon 3037) were purchased from Falcon Plastics (Oxnard, Calif.). Matrigel® was purchased from Collaborative Research Inc. (Bedford, Mass.). Dulbecco's Modified Eagle's Medium/Ham's F12 (DMEM/Ham's F-12) and 10% heat-inactivated fetal bovine sera (FBS) were obtained from GIBCO/BRL (Grand Island, N.Y.). Immunochemical supplies including the Vectastain ABC Kits and 3,3'-diaminobenzidine substrate were purchased from Vector Laboratories (Burlingame, Calif.). Murine monoclonal antibodies were obtained as follows: cytokeratins 8, 18 and 19 (Biodesign clone NCL-5D3; Kennebunkport, Me.); vimentin (Boehringer Mannheim clone V9; Indianapolis, Ind.); a human epithelial cell marker directed against a 200 kilo-Dalton glycoprotein, BMA 180 (Behringwerke AG, Marburg, Germany); pregnancy-associated endometrial $\alpha_2$-globulin ($\alpha_2$-PEG; C6H11, a generous gift from Stephen C. Bell, Ph.D., Departments of Obstetrics and Gynecology and Biochemistry, University of Leicester, Leicester, United Kingdom). Chromatography supplies were purchased as follows: Affi-Gel blue affinity gel, BioRad Laboratories (Melville, N.Y.) and wheat germ lectin sepharose 6MB, Pharmacia Biotech Inc. (Piscataway, N.J.). Nitrocellulose membranes were purchased from Schleicher and Schuell (Keene, N.H.). The Hoeffer Transphor® Blot System was purchased from Hoeffer Scientific (San Francisco, Calif.).

Endometrial Tissues

Human endometrial tissues were used for immunohistochemical localization of PUP-1 and as a source of endometrial epithelial and stromal cells. Tissues were obtained from informed volunteer patients routinely presenting to the physicians in the Department of Obstetrics and Gynecology at the University of Missouri Medical School as approved by the Institutional Review Board using a Pipelle™ endometrial suction curette. The date of the patient's last menstrual period and use of any medication were recorded. Endometrial tissues (n=30) were classified as proliferative (days 4 to 14) or secretory (days 15 to 28) according to the date of their last menstrual period. Endometrial dating was confirmed by histological evaluation by the Pathology Department at the University of Missouri.

Tissue specimens were transported to the laboratory in saline. In the laboratory, a representative portion of each endometrial biopsy was fixed in 10% neutral buffered formalin while remaining tissue was enzymatically dissociated to obtain endometrial stromal cells.

Endometrial Cell Isolation, Purification and Culture

Endometrial epithelial and stromal cells were used for immunocytochemical localization of PUP-1 and as a source of PUP-1 for antibody production. Cells were isolated and purified by enzymatic dissociation and a series of filtrations and sedimentations according to the protocol of [Osteen et al., 1989] with modifications previously described by [Sharpe et al., 1993]. Epithelial and stromal cells were diluted with culture media to a final concentration of $1.0\times10^6$ viable cells/ml. Epithelial cell suspensions (0.4 ml) were plated in Millicelle CM culture inserts coated with 0.2 mL of the extracellular matrix Matrigel® (non-diluted) providing a total of $4\times10^5$ viable cells in a surface area of 78.50 $mm^2$. Aliquots of the epithelial cell suspensions were also plated on plastic cultureware as Matrigel® created an unacceptable background in the immunocytochemical staining process. Other than the elimination of the high background staining, the results of the immunostaining did not vary between the two culture types (matrix vs plastic). Stromal cell suspensions (0.8 mL each) were plated in plastic organ culture dishes for a total of $8\times10^5$ viable cells in a surface area of 176.25 $mm^2$. All cultures were kept in a humidified incubator at 37° C. with 5% $CO_2$. Culture media consisted of phenol-red free DMEM/Ham's F-12 containing 10% heat-inactivated FBS for the first 3 days of culture. By day 4 of culture, the cells had achieved approximately 95% confluence and immunocytochemical studies were performed.

The purity of the cell cultures was immunocytochemically assessed using a variety of intermediate filament protein, glycoprotein and secretory protein markers as previously described by Sharpe et al. [Sharpe et al., 1993]. Antibodies (MAbs) against cytokeratins (for epithelial cells), vimentin (for stromal cells); a human epithelial cell marker directed against a 200 kilo-Dalton glycoprotein, BMA 180 (for endometrial epithelial cells, and for pregnancy-associated endometrial $\alpha_2$-globulin ($\alpha_2$-PEG; for secretory phase endometrial epithelial cells) were used to assess the cells using the Vectastain® ABC Kit as per manufacturer's instructions. Peroxidase activity was demonstrated by incubation with 3,3'-diaminobenzidine substrate yielding a brown intracellular precipitate which confirmed peroxidase staining. Cells were counterstained with hematoxylin. Preimmune rabbit sera substituted in place of primary antibody was used as a negative control in all immunostaining procedures.

Generation of PUP-1 Antibody from Partially Purified PUP-1

For the generation of the PUP-1 antibody, de novo synthesized PUP-1 was partially purified from human endometrial stromal cell culture media. The stromal cells were isolated from a biopsy collected at cycle day 19. The biopsy which weighed 159 mg (wet weight) yielded $7\times10^6$ epithelial cells which were >90% viable and $42\times10^6$ stromal cells which were >80% viable.

Partial purification was achieved by passing the cell culture media containing the de novo synthesized PUP-1 over Affi-Gel blue affinity gel and wheat germ lectin sepharose 6MB. Affi-Gel blue affinity gel was used to remove "contaminating" serum albumin. The wheat germ lectin sepharose, which "sees" certain N-acetylglucosamine and terminal sialic acid residues, bound PUP-1 and other glycosylated proteins to the column matrix. PUP-1 was subsequently eluted with hapten (N-acetylglucosamine). The partially purified proteins isolated by the chromatographic procedures, including PUP-1, were further separated by two dimensional sodium dodecyl sulphate polyacrylamide gel electrophoresis (2D-SDS-PAGE) and then transferred to nitrocellulose membranes at one amp constant current for one hour using the Hoeffer Transphor® Blot System. Proteins transferred to the membranes were visualized by India ink staining. The stained protein "spot" which corresponded to the molecular weight and isoelectric point of PUP-1 ($M_r$ 70,000; pI 5.7) was cut from several nitrocellulose membranes and used as immunogen [Knudsen K A, 1985].

Polyclonal anti-PUP-1 was synthesized "off blot" using a male New Zealand White rabbit and a golf ball-induced granuloma technique [Himmam et al., 1974]. Prior to immunization, ascites fluid was collected for use as a negative control in the immunostaining procedures. An initial immunization of approximately 500 $\mu$g and two subsequent booster immunizations of approximately 250 $\mu$g each of PUP-1 antigen were administered. Immunoreactivity and specificity of the PUP-1 antibody was tested two weeks after each immunization by western blot analysis of 2D-SDS-PAGE separations of endometrial stromal cell culture media.

Immunochemical Staining for PUP-1

Endometrial tissues were formalin fixed, routinely processed, paraffin embedded and sectioned at 3 $\mu$m. After dewaxing, sections were hydrated and equilibrated with phosphate buffered saline (PBS). Endogenous peroxide activity was quenched by treatment with 3% hydrogen peroxide. Immunohistochemical staining was performed with the PUP-1 antibody (1:500) using the Vectastain® ABC kit according to manufacturer's instructions. Peroxidase activity was demonstrated by incubation with 3,3'-diaminobenzidine substrate yielding a brown intracellular precipitate which confirmed peroxidase staining. Sections were then counterstained with hematoxylin. Tissue sections were also incubated with preimmune ascites fluid or phosphate buffered saline substituted in place of primary antibody as negative controls for the immunostaining procedures. No immunostaining was seen in any of these controls which served as the negative staining standard. Photomicrographs were made for documentation.

Near confluent epithelial and stromal cell cultures were immunocytochemically stained for PUP-1 (1:500) using the Vectastain® ABC procedure as described above. Morphometric analysis was used to analyze the proportion of cells exhibiting PUP-1 staining [Weibel E R, 1979]. PUP-1 staining was evaluated in multiple high power fields (400×) of each cell culture. Cells with a brown cytoplasmic precipitate were considered to have stained positive for PUP-1. The proportion (%) of cells exhibiting positive PUP-1 staining was calculated by dividing the number of positively stained cells by the total number of cells counted. Student's t-test was used to confirm statistical significance of staining scores between the proliferative and secretory stages of the menstrual cycle.

RESULTS

Endometrial Tissue Specimens

Thirty specimens were obtained from women with histories of regular menses. The specimens ranged from 29 mg to 250 mg in weight. Additional specimens obtained from women with atypical or absent menstrual cycles were not included in the study.

Endometrial Epithelial and Stromal Cell Isolation and Purification

Endometrial epithelial cells cultured on the extracellular matrices plated on a semipermeable membrane appeared as homogeneous populations of tadpole-shaped cells with prominent, off-centered nuclei and whorling cell-cell processes that wrapped around adjacent cells. Morphometric analysis of the homogeneity of the endometrial epithelial cell cultures revealed that 95–98% of the epithelial cells were decorated with cytokeratin and BMA 180 antibodies; 98% of the secretory stage epithelial cells (but not the proliferative stage epithelial cells) stained with the $\alpha_2$-PEG antibody; and less than 5% of the endometrial epithelial cells stained with the vimentin antibody suggesting limited stromal cell contamination of the epithelial cell cultures.

The endometrial stromal cells displayed a cobblestone mosaic-like, monolayer pattern with distinct cytoplasmic borders which did not overlap and did not demonstrate cell-cell processes. Polygonal-shaped cells with centrally located nuclei were the most numerous in the stromal cell cultures (82%) but elongated spindle-shaped cells with centrally located nuclei and large amounts of cytoplasm (12%) and rounded cells with large nuclei and sparse cytoplasm (3%) were also present. Despite the polymorphic morphology, ≧98% of the cells in the stromal cell cultures were decorated with the vimentin antibody but ≦2% were decorated with the cytokeratin, BMA 180 or $\alpha_2$-PEG antibodies suggesting limited epithelial cell contamination of the stromal cell cultures.

PUP-1 Purification and Antibody Production

Sufficient PUP-1 antigen was obtained from the cycle day 19 endometrial biopsy stromal cell culture media for "off-blot" generation of the PUP-1 antibody. Anti-PUP-1 was present in the ascites fluid obtained after the second booster immunization. A third immunization was given to enhance the response. Specificity of the PUP-1 antibody was determined using Western blot analysis of 2D-SDS-PAGE separated endometrial epithelial and stromal cell culture media. PUP-1 antibody recognized a single protein "spot" corresponding to the molecular size ($M_r$ 70,000) and isoelectric point (pI 5.7) of PUP-1 on the endometrial stromal cell culture media blots. No immunoreactivity was detected on the endometrial epithelial cell culture media blots.

PUP-1 Localization In Human Endometrial Tissues Throughout The Menstrual Cycle The pattern of PUP-1 immunohistochemical localization in paraffin embedded endometrial tissues varied with the stage of the menstrual cycle. Brown intracellular precipitate indicates immunohistochemical localization PUP-1. At cycle day 8, PUP-1 was localized in the endometrial stroma, at cycle day 14, PUP-1 was localized in the endometrial stroma and in the apical region of the ciliated luminal epithelium. At cycle day 19, PUP-1 was localized in the endometrial stroma and apical regions of the glandular and luminal epithelium. At cycle day 25, scant PUP-1 was noted in the stroma with reduced PUP-1 staining in glandular and luminal epithelium when viewed at either 200× or 400×. No immunostaining was observed when preimmune sera was substituted in place of PUP-1 antibody. PUP-1 immunoreactive secretory material was also present in the lumina of the endometrium and glandular epithelium during the mid- to late secretory stage of the cycle but was immunonegative for PUP-1 in the controls stained with preimmune sera in place of the PUP-1 antibody.

During the proliferative stage (days 4–12 evaluated), PUP-1 was localized as a brown precipitate in the endometrial stroma. At cycle day 14, coinciding with the time of ovulation, PUP-1 staining was again documented in the endometrial stroma but also noted in the apical region of the ciliated luminal epithelium. During the mid-secretory stage (cycle days 18–22), PUP-1 was localized in the endometrial stroma and apical regions of the glandular and luminal epithelium. Secretory material immunoreactive for PUP-1 was present in the lumina of the endometrium and glandular epithelium during the mid- to late secretory stage of the cycle but was immunonegative for PUP-1 in the controls stained with preimmune sera in place of the PUP-1 antibody. By cycle day 25, only scant PUP-1 was noted in the stroma with reduced PUP-1 staining in glandular and luminal epithelium as compared to the mid-secretory stage of the cycle. No immunostaining was observed when preimmune sera was substituted in place of PUP-1 antibody.

Localization of PUP-1 in Endometrial Cell Cultures

Distinct subpopulations of the isolated, cultured endometrial stromal cells were decorated with the PUP-1 antibody during both the proliferative (mean±SEM=25.7±2.9%) and secretory (24.6±3.7%) stages of the menstrual cycle. Brown intracellular precipitate indicated immunocytochemical localization PUP-1. PUP-1 staining appeared m ore intense in the spindle-shaped cells and rounded cells than the polygonal-shaped cells. No immunostaining was noted when preimmune sera was substituted for primary antibody. The stromal cells which stained positively for PUP-1 displayed a diverse morphology including all three types of cells observed in the stromal cell cultures. PUP-1 staining appeared more intense, however, in the rounded and spindle-shaped cells than the polygonal-shaped cells. Endometrial epithelial cells were not decorated with the PUP-1 antibody (not shown). No immunostaining was noted when preimmune sera was substituted for primary antibody.

Example 3 demonstrates that the pattern of PUP-1 immunostaining shifts from the endometrial stroma alone during the proliferative stage of the menstrual cycle, to both the endometrial stroma and glands around the time of ovulation and continuing through the mid-secretory stage of the cycle, and eventually dissipates from the endometrium as menses approaches during the late secretory stage of the menstrual cycle. This example also shows that PUP-1 localizes in subpopulations of isolated, cultured endometrial stromal cells but not endometrial epithelial cells.

These observations correlate well with Applicant's previous studies which established that PUP-1 is synthesized and secreted in vitro by cultured endometrial biopsy explants and by isolated endometrial stromal cells, but not epithelial cells, when the tissues are collected during the secretory stage of the menstrual cycle [Sharpe et al., 1993]. Collectively, these observations show that PUP-1 is synthesized by the endometrial stroma and subsequently transferred to the glandular and luminal epithelium for secretion during the secretory stage of the menstrual cycle. The fact that PUP-1 immunostaining was found in proliferative stage endometrial stromal tissues and stromal cells isolated from proliferative stage endometrial biopsies combined with the absence of PUP-1 in proliferative stage endometrial explant or stromal cell culture media further suggests that proliferative stage endometrial stroma may act as a site of storage of PUP-1.

Only distinct subpopulations of the isolated, cultured endometrial stromal cells were decorated with the PUP-1 antibody.

In summary, Example 3 demonstrates that localization of the progesterone-induced uterine protein, PUP-1, in specific cells of the human uterine endometrium is dependent on the stage of the menstrual cycle.

EXAMPLE 4

Example 4 objective was to determine if PUP-1 was present in the decidua and placenta throughout gestation.

Design

Human placental tissues were randomly obtained from first, second and third trimesters of pregnancy.

Materials and Methods

Tissues (n=44) were formalin fixed, paraffin embedded, sectioned at 5 $\mu$m and immunohistochemically stained for PUP-1 using the avidin-biotin peroxidase procedure. Tissue sections were also immunohistochemically stained for cytokeratin and prolactin to identify specific cell populations. The patterns of immunostaining were observed by 3 independent workers.

RESULTS

Syncytiotrophoblast, villous cytotrophoblast and intermediate cytotrophoblast cells were decorated with the cytokeratin antibody but not the prolactin antibody. Decidual cells were decorated with the prolactin antibody but not the cytokeratin antibody and thus could be distinguished from trophoblast cells. Decidual cells and intermediate trophoblast cells exhibited positive PUP-1 immunostaining associated with typical secretory phase endometrial stromal cells. Focal PUP-1 staining was noted in syncytiotrophoblast but not found in endothelium or mesenchyme.

Conclusion

PUP-1, a product of secretory phase endometrial stromal cells, localizes in decidua and trophoblast throughout gestation. PUP-1 localization may represent active decidual and/or trophoblast PUP-1 production or sequestration of PUP-1 from an alternative source, however, the source of PUP-1 but cannot be determined by these studies.

In view of the above experimental data, it must be concluded that there is herein identified a progesterone-induced, estradiol, inhibited uterine protein and functional equivalences thereof. The glycoprotein has been identified in cultured media of isolated and purified endometrial stromal cells but not epithelial cells from human tissues. Generally, there is clearly a role for the use of the glycoprotein in the reproductive process and in the clinical evaluation of endometrial function, differentiation and implantation. Specifically, the glycoprotein and the isolated and purified antibody therefore can be used in the above-described method of determining endometrial receptivity.

Throughout this application various publications are referenced. Full citations for the publications are listed below. The disclosures of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

REFERENCES CITED

Bell S C. Purification of human secretory pregnancy-associated endometrial $\alpha_2$-globulin ($\alpha_2$-PEG) from cytosol of first trimester pregnancy endometrium. Hum Reprod 1986; 1:313–18.

Bolen J W, Hammar S P, McNutt M A. Reactive and neoplastic serosal tissue. A light-microscopic, ultrastructural and immunocytochemical study. Am J Surg Path 1986; 10:34–47.

Cornillie F J, Lauweryns J M, Seppala, Riittinen L, Koninckx P R. Expression of endometrial protein PP14 in pelvic and ovarian endometriotic implants. Hum Reprod 1991; 6:1141–1415.

Critchley H O D, Chard T, Olajide F, Davies M C, Hughes S, Wang H S, et al. Role of the ovary in the synthesis of placental protein-14. J Clin Endocrinol Metab 1992; 75:97–100.

Daly D C, Maslar I A, Riddick D H. Prolactin production during in vitro decidualization of proliferative endometrium. 1983; Am J Obstet Gynecol 145:672–8.

Haining R E B, Cameron I T, Van Papendorp C, Davenport A P, Prentice A, Thomas E J, et al. Epidermal growth factor in human endometrium: proliferative effects in culture and immunocytochemical localization in normal and endometriotic tissues. Hum Reprod 1991; 6:1200–5.

Hillam R P, Tengerdy R P and Brown G L. Local antibody production against the murine toxin of Yersinia pestis in a golf ball-induced granuloma. 1974; Infect Immun 10:458–463.

Isaacson K B, Coutifaris C, Garcia C, Lyttle C R. Production and secretion of complement component 3 by endometriotic tissue. J Clin Endocrin Metab 1989; 69:1003–9.

Joshi S G, Ebert K M, Swartz D P. Detection and synthesis of a progestagen-dependent protein in human endometrium. J Reprod Fertil 1980; 59:273–85.

Joshi S G. Progestin-dependent human endometrial protein: a marker for monitoring human endometrial function. Adv Exp Med Biol 1986; 230:167–86.

Julkunen M, Koistinen R, Suikkari A-M, Seppala M, Janne O A. Identification by hybridization histochemistry of human endometrial cells expressing mRNA's encoding a uterine β-lactoglobulin homologue and an insulin-like growth factor binding protein-1. Mol Endocrinol 1990; 4:700–7.

Julkunen M, Seppala M, Janne O A. Complete amino acid sequence of human placental protein 14: a progesterone-regulated uterine protein homologus to beta-lactoglobulins. Proc. Natl Acad Science USA 1988; 85:8845–49.

Knudsen K A. Proteins transferred to nitrocellulose as immunogens. 1985; Anal Biochem 147:285–288.

Koistinen R, Kalkkinen N, Huhtala M-L, Seppala M, Bohn H, Rutanen E-M. Placental protein 12 is a decidual protein that binds somatomedin and has an identical N-terminal amino acid sequence with somatomedin-binding protein from human amniotic fluid. Endocrinology 1990; 118:1475–8.

Kruitwagen R F P M, Poels L G, Willemsen W N P, Jap P H K, de Ronde I J Y, Hanselaar T G J M et al. Immunocytochemical marker profile of endometriotic epithelial, endometrial epithelial, and mesothelial cells: a comparative study. European J Obstet Gynecol Reprod Biol 1991; 41:215–223.

Lessey B A, Metzger D A, Haney A F, McCarty K S, Jr. Immunohistochemical analysis of estrogen and progesterone receptors in endometriosis: comparison with normal endometrium during the menstrual cycle and the effect of medical therapy. Fertil Steril 1989; 51:409–15.

Maslar I A, Riddick D H. Prolactin production by human endometrium during the normal menstrual cycle. 1979. Am J Obstet Gynecol 1979; 135:751–4.

McRae M A, Newman G R, Walker S M, Jasani B. Immunohistochemical identification of prolactin and 24K protein in secretory endometrium. Fertil Steril 1986; 45:643–48.

Megela C, Balducci M, Bulletti C, Galassi A, Jasonni V M, Flamigni C. Tissue factors influencing growth and maintenance of endometriosis. Ann NY Acad Sci. 1991; 622: 257–65.

Osteen K G, Hill G A, Hargrove J T, Gorstein F. Development of a method to isolate and culture highly purified populations of stromal and epithelial cells from human endometrial biopsy specimens. Fertil Steril 1989; 52:965–72.

Riitten L. Serous ovarian cyst fluids contain high levels of endometrial placental protein 14. Tumor Biol 1992; 13:175–9.

Seppala M, Julkunen M, Riittinen L and Koistinen R. Endometrial proteins: A reappraisal. Hum Reprod 1992; 7:31–8.

Sharpe K L, Bertero M C, Vernon M W. Detection of a progesterone-induced secretory protein synthesized by the uteri but not the endometriotic implants of rats with induced endometriosis. Fertil Steril 1991; 55:403–10.

Sharpe K L, Zimmer R L, Khan R S, Penney L L. Proliferative and morphogenic changes induced by the coculture of rat uterine and peritoneal cells: a cell culture model for endometriosis. Fertil Steril 1992; 58:1220–9.

Sharpe K L, Vernon M W. Polypeptides synthesized and released by rat endometriotic tissue differ from those of the uterine endometrium in culture. Biol Reprod. 1993; 48:1334–1340.

Sharpe K L, Zimmer R L, Griffin W T, Penney L L. Polypeptides synthesized and released by human endometriosis tissue differ from those of the uterine endometrium in cell and tissue explant culture. Fertil Steril 1993; 60:839–51.

Sharpe K L, Zimmer R L and Patel D D. Synthesis and secretion of the progesterone-induced uterine protein, PUP-1, during early pregnancy in the rat. Soc Study of Reprod, 1993; P-233, Fort Collins, Colo.

Sharpe K L, Zimmer R L, Trammell S L and Penney L L. Immunolocalization of progesterone-induced uterine protein, PUP-1, in human endometrium and in endometrial epithelial and stromal cell cultures. Soc Study Reprod, 1994; P-26, Ann Arbor, Mich.

Telimaa S, Kauppila A, Ronnberg L, Suikkari A, Seppala M. Elevated serum levels of endometrial secretory protein PP 14 in patients with advanced endometriosis. Am J Obstet Gynecol 1989; 161:866–71.

Vernon M W, Beard J S, Graves K Wilson E A. Classification of endometriotic implants by morphologic appearance and capacity to synthesize prostaglandin F. Fertil Steril 1986:801–806.

Vierikko P, Kauppila A, Ronnberg L, Vihko R. Steroidal regulation of endometriosis tissue: lack of induction of 17β-hydroxysteroid dehydrogenase activity by progesterone, medroxyprogesterone acetate, or danazol. Fertil Steril 1985; 43:218–224.

Wahlstrom T, Seppala M. Placental protein 12 (PP12) is induced in the endometrium by progesterone. Fertil Steril 1984; 41:781–4.

Weibel E R. Stereological Methods. In: Practical Methods for Biological Morphometry, Vol 1, New York: Academic Press; 1979:33–45.

I claim:

1. An isolated and purified antibody which specifically binds to a purified and isolated human protein, said protein (a) being progesterone induced and estradiol inhibited secretory glycoprotein specifically from human stromal cells of endometrial origin;

(b) having a molecular weight of 70,000 daltons as determined by two-dimensional sodium dodecyl sulphate polyacrylamide gel electrophoresis;

(c) having an isoelectric point of 5.7; and (d) synthesized by human endometrium at times of the reproductive cycle which coincide with fertilization, early embryogenesis, and implantation.

* * * * *